United States Patent [19]

Raines et al.

[11] 4,021,353
[45] May 3, 1977

[54] FLAT PROFILE FILTER

[75] Inventors: Kenneth Raines; George K. Burke, both of Bethlehem, Pa.

[73] Assignee: Burron Medical Products, Inc., Bethlehem, Pa.

[22] Filed: Nov. 20, 1975

[21] Appl. No.: 633,976

[52] U.S. Cl. .......................... 210/448; 128/214 R; 210/446
[51] Int. Cl.² ........................................ A61M 5/16
[58] Field of Search .......... 210/446, 229, 447, 231, 210/448, 461, DIG. 23; 128/214 C, 214 R; 55/159

[56] References Cited

UNITED STATES PATENTS

| | | | |
|---|---|---|---|
| 897,418 | 9/1908 | Sheridan | 210/461 |
| 1,174,784 | 3/1916 | Wasson | 210/446 |
| 2,644,586 | 7/1953 | Cutter | 210/448 |
| 3,615,257 | 10/1971 | Frost et al. | 210/447 |
| 3,709,365 | 1/1973 | Czaplinski et al. | 210/446 |
| 3,841,489 | 10/1974 | Combest et al. | 210/448 |
| 3,882,026 | 5/1975 | McPhee | 210/446 |
| 3,905,905 | 9/1975 | O'Leary et al. | 55/159 |

FOREIGN PATENTS OR APPLICATIONS 157,211  12/1956  Sweden .......................... 128/214 C

*Primary Examiner*—Tim R. Miles
*Assistant Examiner*—Gregory N. Clements
*Attorney, Agent, or Firm*—Shoemaker and Mattare, Ltd.

[57] ABSTRACT

A flat profile filter for IV sets and the like, includes an elongate, flat housing having a filter supporting frame therein defining at least one longitudinally extending, laterally facing opening of greater size than could be accommodated transversely in the housing, and a filter element secured on the frame in spanning relationship to the opening.

6 Claims, 7 Drawing Figures

U.S. Patent  May 3, 1977  4,021,353
FIG.1.
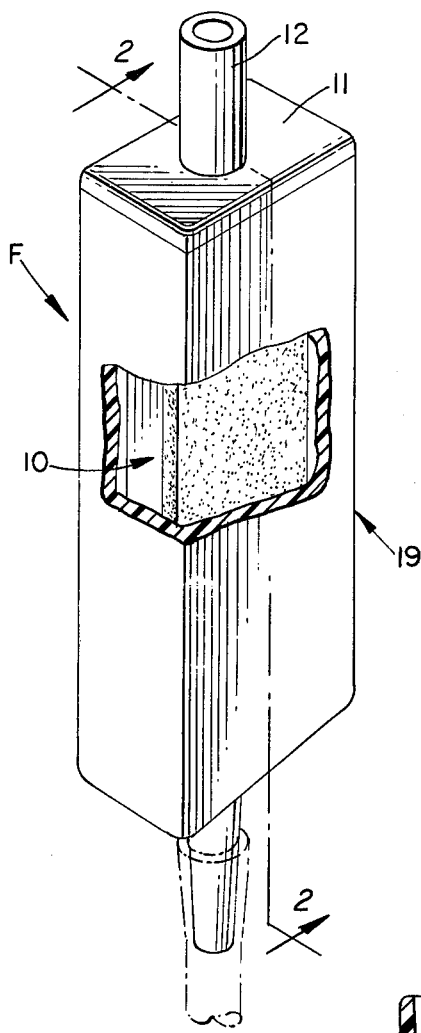
FIG.2.
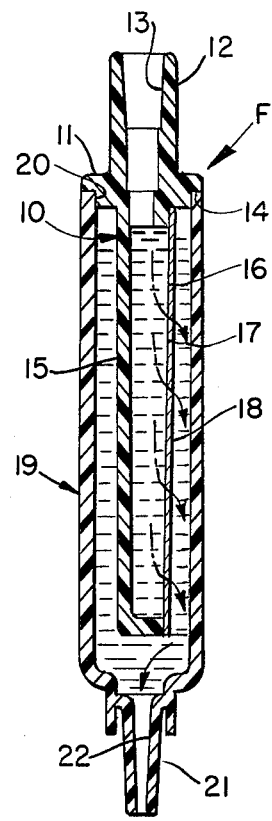
FIG.3.
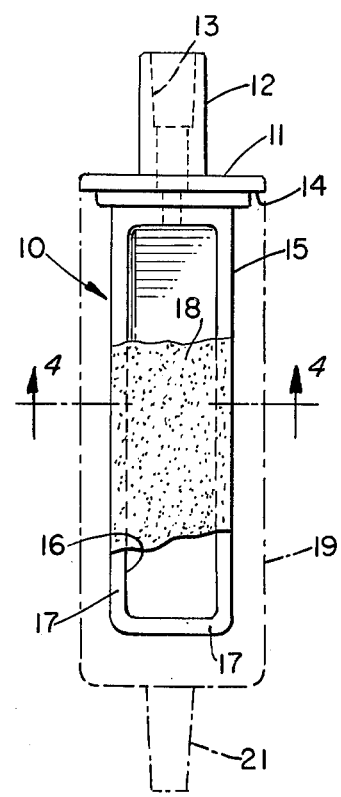
FIG.4.
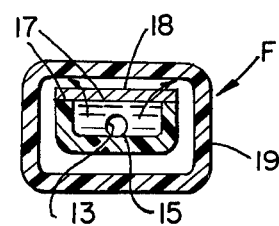
FIG.5.
FIG.6.
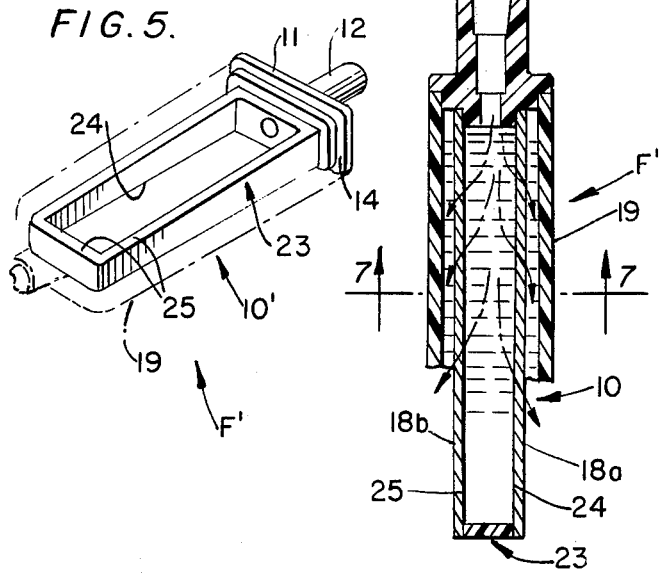
FIG.7.
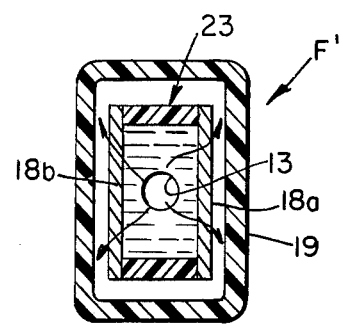

FLAT PROFILE FILTER

BACKGROUND OF THE INVENTION

This invention relates generally to filters for IV sets and the like for intravenous administration of fluids. More particularly, the present invention relates to a filter assembly in which a sub-micron filter element is utilized. Such filters require increased surface area in order to function with standard gravity IV sets. Large filters, however, are bulky and difficult to place near the site of injection. Moreover, in prior art filters for IV sets and the like which utilize sub-micron filter elements, air entrapment is a problem.

With the present invention, a flat profile filter is provided which lends itself to placement near the final section of IV tubing, or in other words, near the site of injection. Further, the present invention enables a much larger filter area to be used than in prior art devices, with a resultant increased flow rate. Additionally, the filter according to the present invention eliminates the problem of air entrapment, and in the present invention, incoming fluid pushes or channels the air ahead of it, pushing the air through the filter and into the housing or case, where it is easily dispersed by tapping or shaking the case or housing. Additionally, a filter in accordance with the present invention can have essentially twice the filtration area within the confines of the same size housing by simply providing a frame having both sides thereof open and sealing a filter element over each opening. Such a double filter assembly is desirable, for example, in situations where adequate flow rates cannot be obtained with a single filter, or when the volume of fluid to be infused exceeds the filtration capacity of the single filter. Further, the elongate flat housing near the injection site provides a gripping means to facilitate manipulation of a needle and the like.

OBJECTS OF THE INVENTION

Accordingly, it is an object of this invention to provide a flat profile filter for IV sets and the like whereby a substantially larger filter area can be provided in less space than is accomplished with prior art devices.

Another object of the invention is to provide a flat profile filter for IV sets and the like which lends itself to placement near the site of injection.

A still further object of the invention is to provide a filter for IV sets and the like in which air entrapment is prevented.

An even further object of the invention is to provide a filter for IV sets and the like wherein the filtration area can be doubled within the confines of the same size housing.

BRIEF DESCRIPTION OF THE DRAWINGS

FIG. 1 is a perspective view, with portions broken away, of a flat profile filter in accordance with the invention.

FIG. 2 is a view in section on a reduced scale, taken along line 2—2 in FIG. 1.

FIG. 3 is a plan view of the filter supporting frame and filter according to the invention, with a portion of the housing shown in phantom lines.

FIG. 4 is a view in section taken along line 4—4 in FIG. 3, showing the filter and frame supported within the housing.

FIG. 5 is a perspective view on a reduced scale of a modified frame for double filter elements in accordance with the invention.

FIG. 6 is a view in section, with portions thereof broken away, of a filter and housing according to the modified form of the invention shown in FIG. 5.

FIG. 7 is an enlarged view in section, taken along line 7—7 in FIG. 6.

DETAILED DESCRIPTION OF THE PREFERRED EMBODIMENTS

In the drawings, wherein like reference numerals indicate like parts throughout the several views, a first form of filter in accordance with the invention is indicated generally at F and comprises a frame 10 having an end wall 11 and an inlet fitting 12 projecting axially substantially from the center of the end wall 11.

The inlet fitting 12 has a bore 13 extending therethrough, and the end wall 11 has an axially forwardly facing shoulder or sealing surface 14 thereon.

The frame also includes an elongate, shallow, generally trough-shaped portion 15, having one open side 16 facing laterally thereof, and bounded by a flat, planar, peripheral filter attaching surface 17.

A filter element 18 of generally rectangular configuration is suitably secured at its peripheral edge to the peripheral surface 17 bounding the opening in the side of frame 10.

In a preferred construction, the filter element 18 comprises a sub-micron filter.

A generally rectangularly shaped housing 19 has an open end 20 thereof suitably secured and sealed to the frame at the end wall 11 thereof, and more specifically, at surface 14 on the forwardly facing portion of end wall 11, and has a tapered outlet fitting 21 on the other end thereof, such as a Luer adaptor or the like, for attachment thereto of a length of IV tubing or other device, as desired or necessary. The outlet fitting 21 has a bore 22 therethrough for flow of fluid from the housing 19.

Preferably, the frame and housing are made of Dural PVC and the frame has an overall length of approximately 2.37 inches and a width measured at the end wall 11 of about 0.75 inch and a depth or height measured at the end wall 11 of about 0.50 inch. Moreover, the filter attaching surface 17 bounds an opening having dimensions of approximately 1.6 inches by 0.375 inch. These dimensions are by way of example only, and are not to be considered limiting.

A modified filter F' is illustrated in FIGS. 5, 6 and 7, and comprises a modified frame 10' having a substantially stirrup-shaped, forwardly extending portion 23 defining two open sides bounded by filter attaching surfaces 24 and 25, respectively, and also having an end wall 11 and inlet fitting 12 as previously described.

A pair of substantially indentical filter elements 18a and 18b are secured to the respective surfaces 24 and 25, as indicated in FIG. 6, for obtaining substantially double the filtration area in the same size housing 19 as obtained with the single filter element 18 in the FIG. 2 embodiment.

In all other respects this form of the invention is substantially identical to that previously described, and the same materials and dimensions may be used in one specific example of the low profile filter.

The filter element or elements can be secured to the frame in any suitable, conventional manner, as by an adhesive or sonic weld or the like.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

We claim:

1. A flat profile filter for IV sets and the like, comprising: a frame having an inlet end with an inlet opening therethrough and an elongate, forwardly projecting filter securing portion having at least one longitudinally extending, laterally facing opening therein, bounded by a substantially flat, planar, filter attaching surface; a flat, planar sub-micron filter element secured at a peripheral edge thereof to the filter attaching surface in spanning relation to the opening, and disposed to one side of the axis of the inlet opening; and a housing secured at one end thereof to the frame and extending in spaced, enclosing relationship to the forwardly projecting portion of the frame and to the filter element, said housing having an outlet opening at its other end for flow of filtered fluid from the housing, means on said housing other end for attachment of a cannula thereto, and said housing defining a low profile hand grip means to facilitate manipulation thereof and to enable said flat profile filter to be easily attached to a patient or the like, said filter element separating the inlet opening from the outlet opening.

2. A filter as in claim 1, wherein the filter securing portion is generally trough shaped in configuration and comprises a longitudinally extending bottom wall having upstanding side walls and an end wall, the side walls and end wall defining said laterally facing opening.

3. A filter as in claim 2, wherein said filter securing portion is integral with the inlet end of the frame.

4. A filter as in claim 1, wherein the filter securing portion comprises a longitudinally extending stirrup shaped frame member having oppositely facing filter attaching surfaces thereon, and a pair of substantially identical spaced apart filter elements secured to the filter securing portion at the oppositely facing surfaces thereof.

5. A filter as in claim 1, wherein the laterally facing opening has a size greater than could be accommodated transversely in the housing.

6. A filter as in claim 1, wherein the frame has two oppositely facing openings therein; and a filter element secured to the frame in spanning relation to each opening.

* * * * *